United States Patent [19]

Tukamoto

[11] Patent Number: 4,508,119
[45] Date of Patent: Apr. 2, 1985

[54] NEEDLE

[76] Inventor: Kenkichi Tukamoto, No. 462-1, Ohaza taki, Fujiwara-machi, Shioya-gun, Tochigi-ken, Japan

[21] Appl. No.: 317,267

[22] Filed: Nov. 2, 1981

Related U.S. Application Data

[63] Continuation of Ser. No. 162,832, Jun. 25, 1980, abandoned, which is a continuation of Ser. No. 857,914, Dec. 6, 1977, abandoned.

Foreign Application Priority Data

Dec. 11, 1976 [JP] Japan ................................ 51-149008

[51] Int. Cl.³ ............................................. A61B 17/34
[52] U.S. Cl. .................................. 128/329 A; 128/1.1; 128/1.3
[58] Field of Search .................... 128/1.3, 1.1, 1.2, 1.4, 128/1.5, 392 A, 303.1, 303.18, 411, 382, 383, 735, 795, 329

[56] References Cited

U.S. PATENT DOCUMENTS

| | | | |
|---|---|---|---|
| 658,027 | 9/1900 | Steiger | 128/1.3 |
| 1,442,051 | 1/1923 | Cummings | 128/1.2 |
| 1,517,861 | 12/1924 | Rosher | 128/1.1 |
| 3,590,821 | 7/1971 | Orlandini | 128/329 A |
| 4,033,054 | 9/1977 | Fukuoka | 128/582 |
| 4,109,661 | 8/1978 | Fukuoka | 128/582 |

FOREIGN PATENT DOCUMENTS

| | | | |
|---|---|---|---|
| 620414 | 9/1935 | Fed. Rep. of Germany | 128/1.2 |
| 2235015 | 1/1974 | Fed. Rep. of Germany | 128/329 A |
| 358456 | 4/1930 | United Kingdom | 128/1.1 |

OTHER PUBLICATIONS

*Radium, Containers & Accessories,* Radium Chemical Co. Inc., 1 E. 42nd St., NY, NY, 5/39.

*Primary Examiner*—Stephen C. Pellegrino
*Attorney, Agent, or Firm*—Bucknam and Archer

[57] ABSTRACT

A needle having at least one of magnetic field and electrostatic field improves effects of acupuncture in Oriental medical therapy. Further, a magnetized and/or electrostatically charged injection needle can be used for so-called "block therapy".

2 Claims, 17 Drawing Figures

NEEDLE

This is a continuation of application Ser. No. 162,832, filed June 25, 1980, now abandoned, which was a continuation of U.S. Ser. No. 857,914 filed Dec. 6, 1977, now abandoned.

SUMMARY OF THE INVENTION

The present invention relates to an improved needle frequently used in Oriental medical therapy, which has at least one of magnetic field and electrostatic field.

More particularly, the present invention relates to an improved needle having at least one of magnetic field and electrostatic field, characterized in that the needle has at least one of (a) a structure in which a part or the whole of the needle (around of which a magnetic field is formed) is permanently magnetized and (b) a structure in which a corpuscular ray emissive nuclide such as $\alpha$-ray or $\beta$-ray emissive nuclide is sealed in a part of the needle, in such a manner that the corpuscular rays do not leak out, so as to form an electrostatic field around the needle.

The present invention further relates to a needle a part of which is provided with a sealed container containing at least one of combinations of an $\alpha$-ray emissive nuclide and an n-type semiconductor substance, and a $\beta$-ray emissive nuclide and a P-type semiconductor substance so that corpuscular rays do not leak out and form an electric field; a needle having both electric field and magnetic field; and a needle further having $\gamma$-ray emissive nuclide so that $\gamma$-ray is emitted weakly in addition to the formation of electric field and magnetic field; and the invention relates to an optional combination of those structures.

The present invention also relates to a magnetized injection needle, an electrostatically charged injection needle or an injection needle having both physical energies to be used in so-called "block therapy" for treatment of a pain.

The present invention further relates to a magnetized ampoule containing a medicinal liquid for block therapy wherein the magnetized needle is used as well as a magnetized box for receiving said ampoule.

DESCRIPTION OF SEVERAL VIEWS OF THE DRAWING

The accompanying drawings are for illustrating embodiments of the present invention.

DETAILED DESCRIPTION OF THE INVENTION AND OF THE PREFERRED EMBODIMENTS

It has been known that acupuncture frequently employed in Oriental medical therapy is effective for diagnosis, remedy, treatment and prevention of various diseases. It has also been known, however, that the needling per se is a strong abnormal stimulation for hypersensitive or weak persons and infants and sometimes exhibits ill effects which offset the intended preferred effects of acupuncture. Further, it has been known that acupuncture therapy exhibits an effects of maintaining homeostasis.

It has been found that, suprisingly, according to the present invention the effect of acupuncture can be improved remarkably by using a needle a part or the whole of which has been permanently magnetized and around which a magnetic field has been formed or a needle in a part of which corpuscular ray emissive nuclide such as $\alpha$-ray or $\beta$-ray emissive nuclide forming electrostatic field around the needle has been sealed so that the corpuscular rays do not leak, or a needle which combines the features of these needles.

The needle of the present invention having electrostatic field (positive electrostatic potential) around the same due to $\alpha$-ray emissive nuclide sealed therein does not exhibit an ionizing tissue destroying effect due to $\alpha$-rays as exhibited by ordinary radium needles. The needle of the invention removes abnormally accelerated electrostatic charge having negative polarity from the outer layer of a cancer cell tissue, regulates electric charge of a plasma membrane and exhibits effects of regulating electromagnetic character, accelerating circulation of the blood in the affected part, raising the sense of heat and relieving the pain of advanced skin cancer.

As a phenomenon of cancerous cells, there may be mentioned their high level of electrostatic charge of negative polarity on the surface as compared with that of normal cells.

If the accelerated negative polarity of the plasma membrane peculiar to the cancer cells is controlled, permeability of the plasma membrane is regulated and specific metabolism system of the cancer can be altered (see No. 27 Japan Cancer Institute, Articles 264 and 274).

From those findings, the therapy with an electrostatic field (electrostatic charge of positive polarity) capable of electric neutralization can contribute to a change in metabolism peculiar to cancer and restorasion of contact inhibition between the cells.

The needle of the present invention having electrostatic field (negative electrostatic potential) formed by sealing of $\beta$-ray emissive nuclide around the same has been attained substantially on the basis of a finding that the effects of anions and negative potential on the living body are sedative and pain-relieving effects.

It has been known that for hypersensitive or weak persons and infants, acupuncture frequently employed in Oriental medical therapy provides on one hand, detestation effect (cause of abnormal stress) which reduces or even cancels the effects of acupuncture.

In such a case, a needle in which a nuclide emitting $\beta$-rays is sealed in a part thereof so that $\beta$-rays do not leak out, the periphery of which needle is electrostatically charged (negative polarity), has a characteristic feature that it can control (or relieve) strange reaction at the time of needling.

In addition, the needle of the present invention having a magnetic field around it regulates reduction in magnetic character peculiar to living body plasma caused by demagnetization, thereby contributing to the maintenance of electron translation system.

One of the keys to the control or stabilization of living body tissue is semiconductive protein which functions in combination with the electron translation system. Namely, the semiconductive protein which functions through electron disappearance from the uppermost band occupied by electrons of insoluble structural protein to an aldehyde acceptor plays an important role in the control or stabilization of living body tissue. However, by the demagnetization of the living body, the electron translation system disappears or is deteriorated.

Even magnetic field on the earth of only about 0.5 Oersted per se poses a series problem with respect to the evolution or existence of living things. From a physical sense that both magnets and electrons are composed of photons, both substances can be regarded to be the same theoretically, since magnetic field is a field of highly dense unpaired electrons which can be considered to be an active electric field.

Inherent intensity of magnetic field of a living body of $10^{-6}$ Oe level is reduced by about 4% by demagnetization by the death thereof (see Erwin Bauer & A. Raskin, Nature, p. 801, Nov. 1936). Further, magnetic susceptibility of cancered cells is far lower than that of normal cells and demagnetization thereof is remarkable (see Frank E. Senftle and Arthur Thorpe, C & EN, p. 38, May 29, 1961). Water contents of substances important in most biochemical reactions are approximately as shown below (given by weight):

| Bones | 49% |
| Muscles | 76% |
| Blood | 79% |
| Lymph | 96% |

Since width of protonic NMR signal of water is far narrower than that of a protonic signal from a living macromolecule and the signals can easily be distinguished from each other, nuclear magnetic resonance (NMR) spectroscopy is utilized for comparative assay of aqueous components of complicated systems (biological systems). Aqueous component of a cancered tissue can be distinguished from that of a normal tissue by measuring the spin lattice-moderating time in the spin echo nuclear magnetic resonance and the spin-spin moderating time. In other words, aqueous component of a cancered tissue has a protonic signal (radio wave) clearly different from that of a normal tissue and the former has a far longer moderating time than the latter due to specific memory or history of water molecules in the cancered tissue, more particularly due to increase in non-orderly degree of hydrogen or increase in Larmor period and reduction in rotational quantum number (see Tumor Detection by Nuclear Magnetic Resonance, Science, March 1971, Vol. 171).

From the fact that dielectric constant and kenematic viscosity of water increase by application of magnetic field and from a finding that parahydrogen is converted to ortho-hydrogen by the application of magnetic field, whereby rotational quantum number is increased by hydrogen, it is apparent that the transformation of the structure of water molecules in the tissue (cancered tissue) in the abnormal (cancering) periods is caused by reduction in magnetic character of the inherent plasma of the tissue and also it is understood that the tissue exhibiting the strange physiological phenomena is under demagnetized condition.

The stimulation by needling is apt to cause a tension and excitation like those of a pain caused by compression of the skin at least instantaneously. The tension invites aggregation (contraction, twitch and stiffness) of the part and the excitation brings about reduction in magnetostatic energy (demagnetization).

Under the circumstances as described above, a technical improvement of the needle has been desired essentially for maintenance of the bioenergy. According to Weber's law and stimulus theory of Hodgkin & Haxlay, the stimulation and excitation impair the equilibrium of so-called Na reversible system (Na-Pump) to alter impedance of the cytoplasmic membrane. Generally, it is said that monovalent alkali ions increase excitation and divalent alkaline earth ions reduce the same. This is due to permeability of the cytoplasmic membrane.

In a suitable range of concentration, an alkali ion reduces stimulus and excitation threshold and an alkaline earth ion increases the same. The decrease in the threshold is accompanied by increase in adaptive constant and the increase in the threshold is accompanied by reduction in the same constant. In this connection, monovalent alkali ions are antagonistic to the divalent alkaline earch ions.

There has been reported an effect of magnetic field on a living body membrane. Gualtierotti, et al. measured amount of Na which permeates through the skin of a frog by using isotope $^{24}Na^+$ in a stationary magnetic field of 650 gausses and recognized a reduction thereof by 10-30%. The effect of the magnetic field disappears if the membrane is deactivated with, for example, potassium cyanide and, also, the effect of magnetic field decreases gradually as Na in the outer liquid is replaced with Li. Accordingly, it is described that the magnetic field directly acts on the transport of Na (see Gualtierotti, T. & Capraro, V: The action of magnetic field on the Sodium transport across the cell membrane. Florkin, M. & Dollfus A. (eds): Life Science and Space Research II, 4th International Space Science Symposium, Warsaw, 1963, Jown Willy & Sons, New York, 1964, 311-316).

Okamoto, et al., measured Ca in the tissue of Citrus unshiu raised under application of stationary magnetic field of 330 gausses and recognized a significant increase by 8% as compared with a control raised without the application of magnetic field (see Bulletin of the Faculty of Agriculture, Shizuoka University, No.16 (1966) pp. 1-6).

From the metabolism of Na and Ca in such a magnetic field, it can be deduced that an improved needle having a magnetic field around it can control the reaction of abnormal pain sensation at the time of needling.

Needles exhibit a specific effect on the maintenance of homeostasis and the needle of the present invention remarkably increases said effect.

The phenomenon of maintenance of dynamic equilibrium by controlling functions of living bodies was proposed first by Canon as homeostasis in 1932.

(I) A needle is made of a super lattice-type alloy such as FePt or CoPt, alnico alloy, K alloy, rare earch-cobalt, barium ferrite, carbon steel, W steel or Cr steel. The needle is then magnetized by a known magnetizing method. Magnetic properties of suitable materials are known in the following table:

| Material | Typical components (%) | Intensity of magnetization $H_{max}$ Oe | Maximum magnetic flux density $B_{max}$ gauss | Residual magnetic flux density Br gauss |
|---|---|---|---|---|
| Carbon steel | C. 1, Mn, 0.5, Fe. residue | 300 | 14,800 | 8,600 |
| W steel | W. 5, C. 1, Fe. residue | 300 | 14,500 | 10,300 |
| Cr steel | Cr. 35, C. 1, Fe. residue | 300 | 13,500 | 9,000 |
| Alnico.1 | Al. 12, Ni. 20, Co. 5, Fe. residue | 2,000 | 12,350 | 7,100 |
| Alnico.2 | Al. 6, Ni. 8, Ti. 8, Co. 35, Fe. residue | 3,000 | 12,800 | 5,800 |
| K. Alloy | Cr. 23, Co. 20, V. 3, Ti. 1, Fe. residue | 3,100 | 12,900 | 6,200 |
| FePt | Fe. 50, Pt. 50 | 1,570 | — | 5,200 |
| CoPt | Co. 50, Pt. 50 | 4,100 | — | 6,300 |

Molecules constituting most of living substances concerning this mechanism can rotate or move in the space, have very characteristic electric and magnetic properties and respond well to even a small outer force (electrostatic field, magnetic field) and thereby being activated.

A direct cause of the activation is anisotropy of dielectric constant and magnetic permeability. A. Sosonosky, et al. proposed the following equation for the relation between the anisotropy and electromagnetic field:

$$[|C| + \epsilon_1 - \epsilon_{11}|]E^2 = (\mu_{11} - \mu_1)H^2$$

in which:
C = constant,
$\epsilon_1$ = dielectric constant in the direction perpendicular to the molecular axis,
$\epsilon_{11}$ = dielectric constant in the direction parallel to the molecular axis,
E = electrostatic field,
$\mu_{11}$ = magnetic permeability in the direction parallel to the molecular axis,
$\mu_1$ = magnetic permeability in the direction perpendicular to the molecular axis, and
H = magnetic field.

In molecules of the above living substance, the asolute value of magnetic susceptibility is minimal in the direction of the molecular axis, and therefore, by application of a magnetic field, molecules and molecular groups are magnetically oriented in the direction of the longer axis and electric susceptibility (intensity of electrostatic field) is increased.

Further, by application of electrostatic field, the magnetic susceptibility (intensity of magnetic field) is increased.

In other words, by application of either magnetic field or electrostatic field, the magnetic field and electrostatic field (electromagnetic index) of the living substance is increased. Therefore, it is understood that the improved needle of the present invention having at least one of the electrostatic field and magnetic field contributes to the activation of the living substance and control of the demagnetizing phenomenon.

Embodments of the present invention will be given below:

(II) Powders of $CsNo_8$ or $CsCl$ are shaped into particles of a diameter of 0.2 mm by using polyvinyl chloride as binder. Cs is converted into $Cs^{185}$ in a nuclear reactor and then they are coated with polyvinyl chloride and each of them is sealed in a part of a needle.

(III) A suitable nuclide such as $Rb^{87}$ is incorporated in polyvinyl chloride and the mixture is injection-molded into filaments under pressure and then coated with polyvinyl chloride. The filament is sealed in a part of a needle.

(IV) A nylon filament is impregnated with a salt of a suitable nuclide such as $Sm^{147}$, then coated with nylon and sealed in a part of a needle.

(V) A small ray source prepared by any of the above methods (II), (III) and (IV) is sealed in a part of a magnetized needle prepared by method (I).

(IV) As nuclides usable in the present invention which emit only $\beta$-rays (100%) weakly but do not emit $\alpha$-rays or $\gamma$-rays, the following nuclides may be mentioned:

| Nuclide | Half-value period (years) | Energy (Mev) |
|---|---|---|
| $Si^{32}$ | 700 | 0.10 |
| $Ni^{63}$ | 120 | 0.067 |
| $Se^{79}$ | $6.5 \times 10^4$ | 0.160 |
| $Rb^{87}$ | $4.7 \times 10^{10}$ | 0.273 |
| $Sr^{90}$ | 28 | 0.544 |
| $Zr^{98}$ | $9.5 \times 10^3$ | 0.063 |
| $Tc^{99}$ | $2.1 \times 10^3$ | 0.292 |
| $Pb^{107}$ | $7 \times 10^6$ | 0.035 |
| $In^{115}$ | $6 \times 10^{14}$ | 0.50 |
| $Cs^{185}$ | $2.0 \times 10^6$ | 0.210 |
| $Re^{187}$ | $6 \times 10^{10}$ | 0.008 |

(VII) As nuclides usable in the present invention which emit only $\alpha$-rays (1100%) weakly but do not emit $\alpha$-rays or $\gamma$-rays, the following nuclides may be mentioned:

| Nuclide | Half-value period (years) | Energy (Mev) |
|---|---|---|
| $Nd^{144}$ | $2.4 \times 10^{15}$ | 1.8 |
| $Sm^{146}$ | $5 \times 10^7$ | 2.55 |
| $Sm^{147}$ | $1.2 \times 10^{11}$ | 2.19 |
| $Sm^{148}$ | $3 \times 10^{18}$ | 2.14 |
| $Gd^{148}$ | 130 | 3.15 |

-continued

| Nuclide | Half-value period (years) | Energy (Mev) |
| --- | --- | --- |
| $Gd^{150}$ | $3 \times 10^5$ | 2.70 |
| $Gd^{152}$ | $1.1 \times 10^{14}$ | 2.15 |
| $Pt^{190}$ | $1 \times 10^{12}$ | 3.3 |
| $Pt^{192}$ | $-10^{15}$ | 2.6 |
| $Pb^{204}$ | $1.4 \times 10^{17}$ | 2.6 |
| $Po^{210}$ | 138 (day) | 5.305 |

(VIII) In sealing the nuclides shown in above items (VI) and (VII), a source of, for example, about 2.1 Mev can completely prevent corpuscular rays (α-rays and β-rays) from leakage with a coating of a thickness of about 0.7 mm of the magnetic substance shown in above item (I).

In case a plastic material is used, the leakage can be prevented with a coating thickness of about 1.4 mm.

As plastic substances that can inhibit the emission of secondary radioactive rays (γ-rays) in the masking of the corpuscular rays, there may be mentioned nylon, rayon, acetate, acryl, polyethylene, Teflon and vinyl chloride. As low specific gravity inorganic substances of low densities, there may be mentioned silicon, selenium, germanium, etc.

(IX) There can be provided a disc-type contact needle of a diameter of 4–6 mm and which may have a very small projection, a grain needle having a very small projection and a ring type contact needle to be used by adhering or fixing (or inserting) the needle to or into a base such as a part of the surface of adhesive plaster, patch or footwear base for continuous or sustaining acupuncture. The ring-type grain needle and disk-type grain needle can apply a specifically enhanced magnetism to acupoints without applying a stimulus due to contact pressure.

Figure 12:
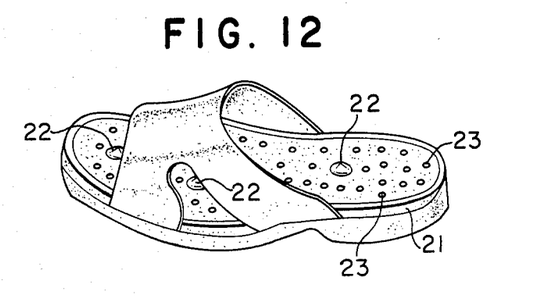
FIG. 12 is perspective view of sandal wherein a contact needle of this invention is fixed or inserted.
Figure 13:
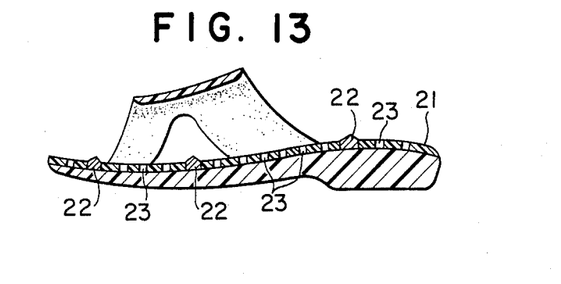
FIG. 13 is side view of the sandal.
Figure 14:
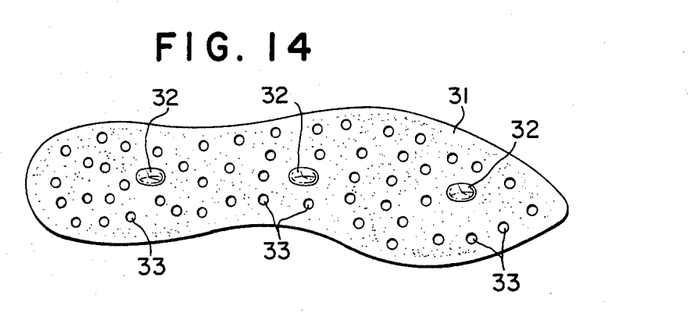
FIG. 14 is plan view of an insole of a shoe wherein a contact needle of this invention is fixed or inserted.
Figure 15:
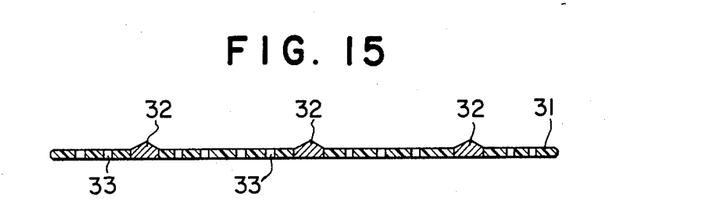
FIG. 15 is side view of the insole.
Figure 16:
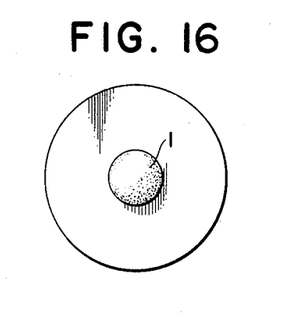
FIGS. 16 and 17 are a plan and side view, respectively, of another embodiment of the disshaped grain (needle) attached to a base.
Figure 17:
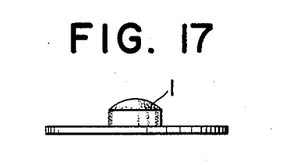

Referring to FIG. 12 and FIG. 13, contact needles 22 having a very small projection in accordance with this invention are fixed to or inserted in a part of the surface of a sandal body 21 which contacts with acupoints of the sole. Symbol 23 in the drawings is a vent hole. Referring to FIG. 14 and FIG. 15, contact needle 32 having a very small projection in accordance with this invention is fixed to or inserted in a part of the surface of an insole body 31 which contacts with the acupoints of the sole. Symbol 33 is a vent hole.

(X) Parts of the surface of footwear base such as sandal and shoe insole to or into which the needle is to be adhered or fixed or inserted are selected so as to correspond to acupoints of the sole such as Yusen (Yungchuan), Nenkoku (Janku), Taikei (Taihsi), Bokushin (Pushen), Shinmyaku (Shenmo), Kinmon (Chinmen), Keikotsu (Chingku), Sokkotsu (Shuku), Ashino Taukoku (Tsu Tungku), Shiin (Chihyin), Kiketsu and Azeketsu.

EXAMPLE 1

$Pb^{86}$ was incorporated in polyvinyl chloride and injection-molded under pressure into filaments. The filaments were coated with polyvinyl chloride and sealed in the head of a No. 3 platinum needle for acupuncture of a length of 6-sun (18.18 cm) in such a manner that β-rays did not leak out to form an electrostatic field (negative polarity) around the needle. Pains at the time of needling with said needle and a conventional No. 3 platinum needle of the same length (control) were examined to obtain the results shown in the following table.

| Needle | Painful | Painless | Total |
| --- | --- | --- | --- |
| Ordinary needle with electrostatic field | 30(6) | 470(94) | 500(100%) |
| Control ordinary needle | 150(30) | 350(70) | 500(100%) |

Both control needles and ordinary needles with electrostatic field (negative polarity) thus selected had ideal sharp ends.

The experiments were effected according to double blank test in which neither operators nor subjects to be needled knew the difference between the needles.

The needle stick was tapped twice and then hit intensely once to complete the insertion. If the subject felt even a slight pain, the result was expressed as "painful" and if the subject felt no pain at all, the result was expressed as "painless".

Order of needling was random according to a table of random numbers to eliminate effect of order.

The tests were repeated 500 times for each sample to obtain results that number of "painful" case of the control needle was 30% and that of the needle applied with electrostatic field (negative polarity) was 6%, a remarkable pain-relieving effect being recognized in the latter.

EXAMPLE 2

D.D.D. Male mice cancered by subcutaneous transplantation of about $4 \times 10^6$ Ehrlich cancer cells were divided into 5 experimental groups of control (not subjected to acupuncture) and A, B, C and D. In four groups A, B, C and D, the following needles for acupuncture were used:

(A) A mixture of nylon and $Sm^{147}$ was injection-molded under pressure into filaments and the filaments were then coated with nylon. The filament was sealed in a globular FePt magnetic needle of a diameter of 4 mm having a small projection in such a manner that α-rays did not leak out, thereby forming magnetic field and electrostatic field (positive polarity) around the needle.

(B) The FePt magnetic needle of above item (A) which was further charged with a known radium ray source so as to emit only γ-rays and to establish a magnetic field therefrom, (C) A needle of the above structure but wherein FePt (magnetic material) was not magnetized so as to emit only γ-rays therefrom.

(D) A magnetic needle of the same structure as in (A) but not containing $Sm^{147}$ and having only magnetic field formed around it.

In each group, the affected part was surrounded by three needles arranged in the form of a triangle having three sides of a length of 3 cm as closely to the part of the subcutaneous transplantation as possible in an early period of the cancer to effect continuous acupuncture by a needle placing technique. The experiments were repeated 10 times using 10 subjects in each case. Increase in growth of the tumor in 7 days was examined in each group to obtain the results shown in the following table. As compared with the control group and radium needle group (C), magnetic needle (A) applied with electrostatic field (positive), magnetic radium needle group (B) and magnetic needle group (D) exhibited a remarkable inhibition of tumor growth.

In terms of percentage, group (C) exhibited 8% increase inhibition and group (A) exhibited growth inhibiting effect of 50%, and groups (B) and (D) exhibited the effect of 17% as compared with the control.

| Number of experiments | Increase in amount of tumor in 7 days (g) | | | | |
|---|---|---|---|---|---|
| | Control | A | B | C | D |
| 1 | 1.5 | 0.2 | 1.3 | 1.4 | 1.0 |
| 2 | 1.3 | 0.3 | 0.8 | 1.4 | 1.2 |
| 3 | 1.0 | 0.5 | 1.3 | 0.9 | 1.55 |
| 4 | 1.2 | 0.4 | 1.2 | 1.3 | 0.2 |
| 5 | 0.8 | 0.7 | 0.6 | 0.7 | 0.75 |
| 6 | 0.75 | 1.1 | 0.2 | 0.85 | 0.6 |
| 7 | 1.5 | 1.3 | 0.75 | 1.3 | 1.2 |
| 8 | 1.45 | 0.9 | 1.2 | 1.65 | 0.8 |
| 9 | 1.6 | 0.5 | 1.55 | 1.3 | 1.3 |
| 10 | 1.9 | 0.7 | 1.0 | 1.2 | 1.3 |
| (Average) | 1.30 | 0.66 | 1.08 | 1.20 | 1.08 |

Further, the above described ill effects in acupuncture can be eliminated by using a needle a part of which is provided with a sealed vessel in which at least one of a combination of an $\alpha$-ray emissive nuclide and an n-type semiconductor substance and a combination of a $\beta$-ray emissive nuclide and a P-type semiconductor substance is sealed in such a manner that the corpuscular ionizing rays do not leak out; the same needle further provided with magnetic field; the same needle further carrying a $\gamma$-ray emissive nuclide to form both electric field and magnetic field and to emit $\gamma$-rays weakly, and a needle having any combination of the above structures.

It has been known that both P-type and n-type semiconductors are electrically neutral in the absence of electric field but as the n-type semiconductor loses electrons, the positive potential of the whole is increased; as the P-type semiconductor takes electrons, the negative potential of the whole is increased; if the P-type and n-type semiconductors are bonded together to form polar electric fields at both ends thereof, a rectifying effect is brought about; and if P-N contact face is irradiated with $\beta$-rays uniformly, a hole reacts with the electron at the contact face to leak the electric current.

According to the present invention, a needle is magnetized by carrying ionizing corpuscular ray (such as $\beta$-ray or $\alpha$-ray) emissive nuclide on n-type and P-type semiconductor substance to form an electric field of positive or negative potential or terminal-connection of them and the same is carried by the needle.

Further, according to the present invention, a magnetic material such as alnico, permalloy or barium ferrite is used for the preparation of the needle. The magnetic material is subjected to a magnetization treatment to convert it to a permanent magnet. Alternatively, a permanent magnet is carried on the needle together with a semiconductor having positive or negative potential or current-leaking electric field to form the charged needle which establishes a magnetic field.

If a P-type semiconductor substance carrying a $\beta$-ray emissive nuclide is charged in the head stick of the needle so that $\beta$-rays do not leak from the needle stick or needle head or if cathode of said P·$\beta$-n·$\alpha$ terminal-connecting (junction) electric field is formed in the needle stick to negative charge the needle body, stimulation reaction accompanied by abnormal sensation of pain which may occur at the time of needling can be relieved.

The charged needle of the present invention in which an n-type semiconductor substance carrying an $\alpha$-ray emissive nuclide is sealed in the head of needle stick or in which anode of the P$\beta$-n$\alpha$ junction electric field is formed in the needle body so that $\alpha$-rays do not leak from the needle stick or needle head do not exhibit ionizing destruction action by $\alpha$-rays on the tissue as is observed in acupuncture with radium needles. The needle eliminates abnormally accelerated negative charge of the surface layer of the cancer cell tissue non-destructive to alter the charge of the membrane. If the needle is used for the treatment of advanced skin cancer, increase in electromagnetic character, acceleration of circulation of the blood, raising the sense of heat and relief of the pain by orientation polarization of biocolloid at the cancered part can be expected by the application of electric field (positive) and acupuncture effect as described above.

Conventional medical treatment of cancer with a radioactive needle (such as radium needle, californium needle or the like), a radon seed (a gold capsule in the form of a seed containing radioactive radon) or another general sealed small ray source ($\gamma$-ray, neutron ray) is significant for ionizing destruction of solid cancers. However, this method of medical treatment has demerits in that oxides and peroxides are formed secondarily, leucocytes in the blood around the cancered tissue are reduced in number and there is a fear of cancering normal tissue. These defects bring about a fatal result to a living body.

As one of effects of application of magnetic field on a living body, it has been known that leucocytes are increased remarkably in number after the magnetic field is removed from the living body.

Further, it has been reported that if a stress reaction occurs due to a pain, secretion of cortisone from the adrenal cortex is enhanced to raise cortisone concentration in the blood to about 20 times as high as normal value in five minutes. By the increase of cortisone, the formation of T-lymphocytes is suppressed to decrease the leucocyte number in the blood to one half in several hours, and the thymus forming T-lymphocytes is also affected and 10–14 days are required for recovery of the thymus (see Science, Aug. 8, 1975, and J. Am. Med. Assoc. Aug. 18).

From the viewpoint that an immunological watching system is present in a living body, which recognizes cancered cells and destroys the cells immediately, a physiological disorder, particularly the reduction of T-lymphocytes in number, due to the abnormal stress inhibits the carcinostatic function of the watching system. It has been proved that if the magnetic field, in which electrons are arranged in order, is lost, the cells can no more be controlled and are attacked by cancer.

Accordingly, a needle having a sealed small ray source which emits $\gamma$-rays or neutron rays weakly and which is applied with suitable electric field and permanent magnetic field is characterized in that it is capable of altering the radioactive ray-susceptibility of a living body and also of reducing the fear of cancering of the tissue around the affected part.

From the fact that number of rotary quanta is increased by conversion of para-hydrogen→ortho-hydrogen known by inspection of chemical activity of the molecules and crystal surfaces, it may be construed that transformation of the structure of molecules of tissue water is nothing but a change in the magnetic character.

More specifically, hydrogen molecules include two isomers, i.e. para-isomer and ortho-isomer, and these isomers are generally present in a ratio of 1:3, and transformation of these isomers is practically impossible without use of a catalyst. Probability of this transformation is substantially zero from viewpoint of the quantum theory. However, this transformation is made possible under application of a magnetic field (see U. Farkas & Z. Sachsse, Physik. Chem. (B), 23, 1 (1933); and Farkas, Orthohydrogene, Parahydrogene and Heavy Hydrogen (1935)).

Accordingly, the fact that the applied magnetic field makes changes in the symmetry of the inherent function by changing the nuclear spin of hydrogen molecules from ↑↓ to ↑↑ means that accompanying deformed waves and increase in number of rotatory quanta (increase in density of ortho-hydrogen) exert a great influence on proton spectrum, hydration and transformation of the structure of water.

All growth phenomena taking place on the earth involve a lethal factor therein. More specifically, when a living tissue continues growth, an optimum condition for survival of the tissue system defined by the interrelation with the environment is reached. However, at this point, the tissue system generally fails to perform self-control, and therefore, the optimum condition is passed and a climax condition is finally reached. Consequently, the normal growth of the tissue system is inhibited and degeneration begins and the tissue system tends to be transformed to a tissue system in which a different metabolism is prevalent.

The harm of peroxides and related phenomena is chemically fatal to living bodies living in an oxygen-containing atmosphere. They do various harms to living bodies through various mechanisms to cause ataxia of various functions of living bodies and reduction in defense strength of living bodies to bring about cancers (see Kazuo Fukuzumi, Oil Chemistry 14, 119 (1965); and Hiroyuki Kono, Journal of Japanese Association of Eastern Medicine, 21 (4), 195 (1971)).

The increase in oxides and peroxides (both be de-electronation) bring about a dilution effect on electric field and magnetic field (about $10^{-6}$ –$10^{-7}$ gauss) of the plasma inherent to a living body.

It is considered that an orientation-polarized biocolloid exhibits paramagnetism. However, paramagnetic energy is very low. The maximum magnetic moment of a paramagnetic ion is an applied magnetic field of less than about $10^8$ Oe is:

$$5.4 \times 10^{-20} \text{ erg/Oe.}$$

Accordingly, potential energy thereof is:

$$\begin{aligned} m.H &= 5.4 \times 10^{-20} \text{ erg/Oe} \times 10^8 \text{Oe} \\ &= 5.4 \times 10^{-17} \text{ erg} \end{aligned}$$

On the other hand, thermal energy at an ambient temperature is:

$$K \cdot T = \sim 4 \times 10^{-14} \text{ erg.}$$

Therefore, potential energy of paramagnetism is at most ¼ of the thermal energy. Accordingly, in a phenomenon such as orientation of the biocolloid in which it is susceptive to a thermal interference magnetic field interference effects on the orientation polarization substance are hardly expectable except for quantum-mechanical effect and, as for diamagnetism, it is considered that magnetic moment is insignificant, since it is less than 1/100 of the paramagnetism.

However, in living substances such as cell membranes, liquid crystals which respond to even a very small outer force are present (see F. T. Stewart, Ordered Fluids and Liquid Crystals, 141 (1966); The Journal of the American Oil Chemists' Society, Vol. 45, 120 (1968)).

Since constituent molecules of a liquid crystal can rotate or migrate in a space, the liquid crystal has very characteristic electric and magnetic properties.

For example, cholestric mesophase is converted to nematic mesophase under application of an electrostatic field or a magnetic field. Since the spiral structure is converted to a structure in which molecules are parallelly oriented, this change is very violent, and further, this great change of the molecular orientation or arrangement is caused by application of a relatively small magnetic or electrostatic field.

In case of a typical model, the elastic energy of torsion is about $4 \times 10^{-8}$ Cal./M, and it is about $10^{-5}$ of the energy necessary for arranging all of the molecular axes. According to Meyer, electrostatic field (Ec) and magnetic field (Hc) causing the transition are expressed as follows:

$$Ec = \frac{2\pi}{P_o}\left(\frac{K_{22}}{\Delta Xe}\right)^{\frac{1}{2}}, \text{ and}$$

$$He = \frac{2\pi}{P_o}\left(\frac{K_{22}}{\Delta Xm}\right)^{\frac{1}{2}}$$

in which:
$P_o$ = spiral pitch at Ec=O and Hc=O,
$\Delta Xe$ = anisotropy of electric susceptibility,
$\Delta Xm$ = anisotropy of magnetic susceptibility $K_{22}$ = torsion elasticity
(See R. B. Meyer, Applied Physics Letters, May 1, 1968).

In the above equations, if $P_o = 5{,}000$Å, anisotropy $\Delta\epsilon$ of dielectric constant $\simeq 1.0$, anisotropy $\Delta\mu$ of magnetic permeability $\simeq 1 \times 10^{-4}$ and $K_{22} \simeq 10^{-6}$ dyne, Ec is nearly equal to $10^5$ V/cm and Hc is equal to $10^5$ Oe, which values are substantially in agreement with found values.

Also Gennes stated, as a result of calculation of the phase transition by application of magnetic field, that if Po—1 μm and XX$\simeq 10^{-5}$, a value of Hc$\simeq 1.5 \times 10^{-4}$ Oe is given (see P. G. De Gennes, Solid State Communications, Vol. 6, p. 163, 1968).

It has been known that viscosity (kinematic viscosity) of water is also increased by application of magnetic field of approximately $10^2$–$10^3$ Oe (see Data of Meeting for Presentation of Research Results sponsored by Japanese Association for Advancement of The Mining Industry), p. 3, 1964).

Molecules of living substances constituting liquid crystals of living bodies are oriented and polarized under application of an unimaginably small electric field or magnetic field, and direct causes of this phenomenon are anisotropy of the dielectric constant and that of magnetic permeability. Under application of magnetic field, molecules and groups of molecules are magnetically oriented in the direction of the longer axis and the electric susceptibility is increased as described above Further, by application of electric field, electric dipole-forming rate is increased and potential is increased, thereby increasing also magnetic susceptibility.

On the contrary, if oxidation and peroxidation (each being deelectronation) are accelerated, intensity of the electric field is reduced, which in turn, causes reduction in intensity of the magnetic field. Namely, deelectronation results in demagnetization and demagnetization results in deelectronation.

Since all substances have an inherent magnetic character, each cell, tissue, organ or other organic body must have its inherent magnetic field, and in view of the fact that levels of energies of chemical linkages in molecules regulate possibiliites of interrelations among respective substances, it can be considered that levels of energies of molecular linkages, which are to express magnetic characteristics of substances, are changed, in turn, by variation of magnetic characteristics in substances and are influenced by transformation of substances.

Also an electric current forms a magnetic field, and a magnet can be regarded as an assembly of small currents. In contrast, quantity of magnetism differs from quantity of electricity in the point that it is not an unvariable quantity inherent to a substance, and the presence of a quantity of magnetism is a statistical phenomenon caused by ununiform distribution of particles having a magnetic moment. It is apparent that a small magnetic field formed by particles having a dipole moment in a certain system, namely the magnetic character of a substance, is influenced by the temperature, the external magnetic field (outside the system), the force of the electric field and the directivity to the directions of these magnetic and electric fields. An electric potential is generated as a result of chemical reactions of substances caused by change in magnetic characters of the substances, and once the electric potential is generated, it comes to have influences on the magnetic character of the substance. Thus, an unseparable unit body, namely an electromagnetic state of a living tissue or a polarity, is generated through the action of a living body. On the one hand, the polarity can be regarded as expressing a certain property involved in transformation of an organic substance, and on the other hand, the polarity per se clarifies the property of transformation of the substance. The change in magnetic character of a substance and hence, the change is polarity are naturally influenced through the living actions of the organic body.

Chinese medicinal needle treatment (acupuncture) per se is now in the limelight as an effective means of cancer therapy (see Natural Demonstration, 1974 published by Shanghai People's Publishing Co.).

Generally, amount of amino acids (glutamic acid, aspartic acid, leucine, etc.) is increased to 3–4 times the original amount by acupuncture (see Medical Science of Acupuncture, p. 127 published by Sogen-sha in 1956).

Like the biocolloids, amino acids thus formed are activated by deformed waves of the liquid crystals oriented and polarized by application of magnetic field, thereby contributing to activation of basal plasmas (electric and magnetic field) inherent to living bodies and also exhibiting a remission effect on various strange phenomena caused by deelectronation and demagnetization (formation of perioxides) in living body functions.

From the above findings, it is understood that the magnetized needle (comprising needle head and stick) made of a magnetic material exhibits significant effects.

After the radon seed was found in 1926, technical improvements have been accumulated gradually. In Japan, about 45,000 cases (1970) of small ray source therapy were effected and they succeeded in saving the lives of numerous cancer patients with such cancers as cancer of the tongue. According to the needle of the present invention having also magnetic field effect, rate of healing can be enhanced further.

The needle of the present invention has also a high molecular-biological significance. As one of the biologically stable mechanisms of mitosis of cells, there has been known metabolish of nucleic acids (DNA and RNA).

DNA is discontinuously synthesized, and RNA is first synthesized prior to the synthesis of DNA (see Reiji Okazaki, Molecular Biological Laboratory, Nagoya University Collection of Experimental Reports, 1972).

By V. U. Strekova, G. A. Tarakanova, V. P. Prudnikova and U. I. Novitskiiv, it was confirmed that RNA is remarkably increased in a living body by application of a magnetic field (see Fiziol. Past 12; 920–929, 1965).

Peroxidized state (deelectronated and demagnetized state) in the living bodies inhibits the duplicating mechanism by nucleic acids (see Lester Backer and James Smith, Laurence-Barkly Laboratory, California University; Bulletin of American Science Academy, 1974).

It will readily be understood that electromagnetic fields are necessary for continuing reproduction in living bodies without exerting harmful influences on nuclic acids from Szent-Gyorgi's report. It is considered further that electromagnetic field environments (a state applied with electric and magnetic fields) sufficient not to lose control, normal metabolism of nucliec acids is enhanced and metabolism of cancering nucleic acids is converted to metabolism of anticarcinogenic nucleic acids. This fact is supported sufficiently by the following examples:

(1) Mice inoculated with Ehrlich's Adenokarzinoma were exposed to a magnetic field for 8 hours a day. Growth of the tumor of the mice was smaller than that of the control (1940, Lenzi, M.).

(2) In 6 cases of white mice inoculated with T1246 adenocarcinoma, the tumor disappeared in 5 cases by treatment in a magnetic field and complete recovery was obtained in 4 cases, while death rate in 16 control mice was 100% (1948, J. Barnothy, Hungary).

(3) $C_8H$ Mice inoculated with $C_8HBA$ mammary tumores were treated in a magnetic field and exhibited an increase in surviving period by 44.9%. No metastasis was recognized by pathological experiments (1955, Barnothy, Evanston, Ill.).

(4) $C_8H$ Mice inoculated with H 2712 adenocarcinoma were treated in a magnetic field. 20 Percent of the cases lost the tumor and recovered (1957, J. Barnothy, Evanston, Ill.).

(5) $C_8H$ Mice treated in a magnetic field for 4 weeks in their early days exhibited increase in running power by 40% and reduction in amount of food consumption by 14% and they looked surprisingly young in their old age. Start of spontaneous tumors of the breast frequently occurring in $C_8H$ mice was later than that of normal case by 20% (1956–1959, J. Barnothy, Evanstone, Ill).

(6) 78% Of mice affected by leukemia and treated in a magnetic field recovered, while death rate in the control was 100% (1959, W. Kirsten, Chicago, Ill.).

(7) T 2146 Adenocarcinoma planted in mice was placed in a magnetic field and 30% of them were cured completely, while in control group, death rate was 100%. Mice inoculated with $C_8 HBA$ mammary adenocarcinoma had an average surviving period in a magnetic field longer than that of control (outside the magnetic field) by 44%. Thus average tumor weight at the time of death was 35% based on that of the control (1959, 1962, Barnothy, J. M.).

(8) Ascites tumor (Sarcoma 37) raised in a suspension drop type culture medium exhibited a complete cell degeneration after allowing it to stand in a magnetic field for 18 hours. Also, delay of introduction of spontaneous tumor was recognized (1961. The First Biomagnetics Symposium, U.S.).

(9) The growth of spontaneous mammary tumors of $C_8H$ mice is terminated by treatment in a magnetic field (1961, J. Barnothy, Chicago, Ill.).

(10) One of the primary factors for anticarcinogenic effects of a magentic field is that tissue-resolution is inhibited in a magnetic field.

If mice having tumors were exposed to magnetic field prior to the inoculation, surviving period is prolonged (1960–1964, Gross).

(11) If muscular tissues are placed in a magnetic field, infiltration of the tumors inoculated in the muscular tissues are inhibited to prolong average surviving period of the mice and implantation is reduced (1963–1964, Barmothy, M.).

(12) As compared with normal healthy tissues, tumors are highly susceptible to a magnetic field and magnetic effects on tumors are obtained also in spontaneous tumors (1961, Mulay, 1964, Verner, Nutini).

(13) $C_8H$/HeJ Mice transplanted with 10,000,000 mammary tumor (H 2712) cells which had been exposed to a magnetic field for 20 minutes survived for only 7.9±1.4 days. On the other hand, $C_8H$/HeJ mice exposed to a magnetic field after the transplantation survived 18±1.3 days in average.

After the transplantation followed by formation of palpable tumors (i.e. after 48 hours), the tumor tissues in the bodies were exposed to a magnetic field after 72 hours and 96 hours each for 20 minutes. Average surviving period was 21.11±2.0 days. Thus, an apparent inhibition effect of the magnetic field was recognized (see Medical Department, Ohio University, Cancer, August 1971).

As small ray source substances suitable for making a radioactive medical appliance emitting γ-rays, neutron rays, etc., there may be mentioned radium, cobalt[60] and californium[252]. N-type and P-type semiconductor substances, germanium compounds, silicon compounds and selenium compounds are suitable.

EXAMPLE 3

Figure 1:
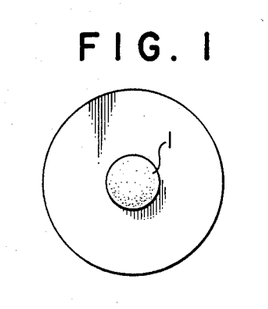
FIGS. 1–2 are a side view and plan view, respectively, of a case wherein a disc-shaped grain (needle) is attached to a base.
Figure 2:
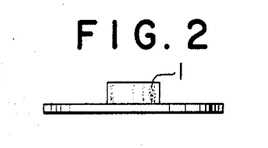
Figure 3:
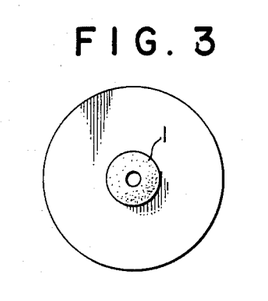
FIGS. 3–4 are a side view and plan view, respectively, of a case wherein a ring-shaped grain (needle) is attached to a base.
Figure 4:
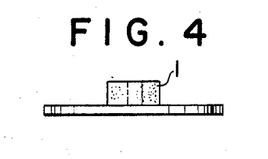
Figure 5:
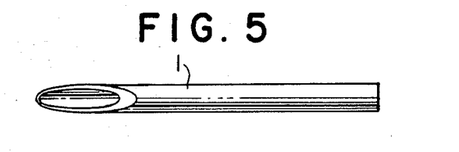
FIGS. 5–6 are a side view and plan view of a slender cylindrical needle, which is magnetized, having a sharp end.
Figure 6:
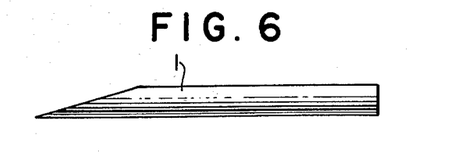
Figure 7:
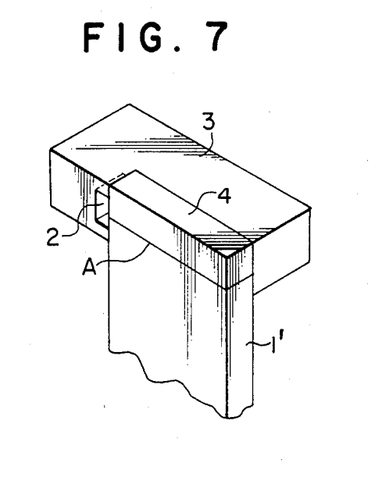
FIG. 7 is a view of the head of an electromagnetic needle.

A needle for acupuncture which was used in this example will be described with reference to symbols given in FIG. 7.

Rb[87] was incorporated in polyvinyl chloride and injection-molded into filaments (2) under pressure. The filament was carred on (or placed on) a germanium P-type semiconductor (4) in such a manner that β-rays did not leak out. The thus charged substance was fixed at the head (A) of a needle for acupuncture together with an alnico magnet (3). Thus obtained No. 3 platinum ordinary needle 1' applied with an electric field (negative) and magnetic field of a length of 6-sun (18.18 cm) exhibited the results shown in the following table, as compared with ordinary No. 3 platinum needle of the same length:

|  | Painful | Painless | Total |
| --- | --- | --- | --- |
| Ordinary needle magnetized and charged (negative) | 25(5) | 475(95) | 500(100%) |
| Ordinary needle (control) | 150(30) | 350(70) | 500(100%) |

Thus selected control needles and charged needles both had ideal sharp ends. The needle was tapped twice and then hit intensely once to complete the insertion. If the subject felt even a slight pain, the result was expressed as "painful" and if the subject felt no pain at all, the result was expressed as "painless".

Tests were repeated 500 times for each needle to obtain the results as shown in the above table, namely, painful cases in the magnetized and charged (negative) needle were 5%, while those of the control were 30%, a remarkable pain-relieving effect being obtained in the present invention.

EXAMPLE 4

D.D.D. Male mice cancered by subcutaneous transplantation of $4 \times 10^6$ Ehrlich cancer cells were divided into four groups A, B, C and D. The following needle for acupuncture were used in each group. The needle will be described with reference to symbols given in FIG. 8.

Figure 8:
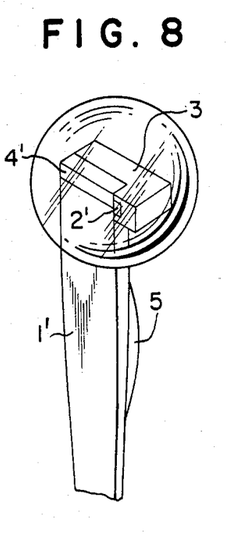
FIG. 8 is an explanatory view of the head of a radioactive electromagnetic needle.

(A) Polyvinyl chloride incorporated with Sm[147] was injection-molded under pressure into small pieces. The pieces were covered well with polyvinyl chloride to obtain pieces 2'. The piece 2' was placed (charged) on a germanium n-type semiconductor 4' to positively charge the semiconductor. An alnico magnet 3 was attached thereto. The whole was covered with platinum 1' to obtain a needle having a sealed vessel of a diameter of 6 mm from which α-rays did not leak out and also having a magnetic force. Three needles were used in each case.

(B) The needle of above item (A) which was further filled with a known radium ray source 5 so that it emitted γ-rays in addition to magnetic force. Three needles were used in each case.

(C) Three needles the same as those in above iems (A) and (B) containing a platinum sealed container of a diameter of 6 mm but not containing alnico magnet or n-type semiconductor, in which only radium ray source 5 the same as in (B) was placed in the position shown in the figure.

(D) Control in which no needle was used.

In each experiment, the affected part was surrounded by three needles (one needle from each of the three groups) arranged in the form of a triangle having three slides of a length of 3 cm as closely to the part of subcutaneous transportation as possible in the early period of the cancer. The experiments were repeated 10 times using 10 subjects in each group. Increase in growth of the tumor in 7 days was examined in each group to obtain the results shown in the following table. It was recognized that as compared with control group (D) and radium needle group (C), group (A) of magnetic, positively charged needle applied with a magnetic field and group (B) of magnetic, positively charged radium needle exhibited a remarkable inhibition of tumor growth.

In terms of percentage, group (C) exhibited an 8% increase in inhibition and groups (A) and (B) exhibited tumor growth-inhibiting values of 50% and 40%, respectively, as compared with control group (D).

| Number of experiments | Increase in amount of tumor in 7 days (g) | | | |
|---|---|---|---|---|
| | Group (A) | Group (B) | Group (C) | Group (D) |
| 1 | 0.3 | 0.33 | 1.4 | 1.5 |
| 2 | 0.2 | 0.4 | 1.4 | 1.3 |
| 3 | 0.4 | 0.66 | 0.9 | 1.0 |
| 4 | 0.5 | 0.5 | 1.3 | 1.2 |
| 5 | 1.1 | 0.86 | 0.7 | 0.8 |
| 6 | 0.7 | 1.2 | 0.85 | 0.75 |
| 7 | 0.8 | 1.4 | 1.3 | 1.5 |
| 8 | 1.3 | 1.09 | 0.65 | 1.45 |
| 9 | 0.7 | 0.83 | 1.3 | 1.6 |
| 10 | 0.5 | 0.65 | 1.2 | 1.9 |
| (Average) | 0.65 | 0.79 | 1.20 | 1.30 |

Against a pain phenomenon the mechanism of which has not been clarified yet, local anesthetics such as xylocaine are administered through acupuncture with a needle to acupoints in Chinese medical treatment according to so-called "block therapy". It has been know, however, that injections are a major cause for diseases caused by medical treatments such as amyotropy and there has yet been proposed no solution. It is expected that prevention of prognostic symptoms due to the injection can be achieved by magnetizing or electrostatically charging the injection needle or by applying both physical energies thereto. For example, physiologically active substances (ions) in an injection solution may be deactivated and modified (oxidated and demagnetized) as time elapses. In addition to influence of a magnetic field on the ions, it is considered that a solvent (water) per se is influenced by the magnetic field. More particularly, dipole moment of water molecules is influenced by the magnetic field.

Water is made of H and O combined by covalent bond. Water has a V-shaped molecular structure (H—O—H) having an O-band angle of 104°. The water molecules form a random cluster (polymer) of a certain degree. In case the magnetic field is perpendicular to a stream of water, if the movement of water molecules (i.e. electric charge) is replaced with electric current, water receives a force perpendicular to the water steam by the magnetic field. Since all ionic bondings are effected through the water molecules, it is considered that a change in the water cluster naturally exerts an influence on the shape of ionic bond.

It was recognized that water applied with a magnetic field exhibits a highly significant biological activity equivalent to that of water obtained from thawed ice or snow by the Arctic Laboratory of U.S.S.R. from the fact that a remarkable propagation of plankton was observed when ice and snow thawed. Hence, the water is called magnetized water. The magnetized water prominent as a precursor of the recent magnetobiological findings increases the agricultural yields to 2–3 times as much as ordinary yields; enhances growth of chickens, egg-laying rate of hens and amount of cow's milk; and activates (rejuvenates) both human beings and animals, because a specific structure (i.e. magnetized lattice space; it has also been recognized that the water loses its activating effect if it is thawed by heat or boiled) of a diameter of about 20 Å formed in the water by the application of magnetic field permeates readily through membranes of living body tissues into the various tissues. This magnetic water contributes greatly to an increase in normal metabolism of the whole tissue system.

Such an enhancement of normal physiological functions is due to the fact that the specific structure of the water applied with a magnetic field is extremely flexible and molecules of living bodies are arranged ideally without any damage while latent living functions are maintained. It has been also recognized that molecules of living bodies are destroyed and the tissues are deteriorated by the action of water in which the specific structure is deficient or lost (see BO □A BO BCE □EHHON, B□A □NMNP ʃ □ EP □□O □bN, N3 □ATE□bCTBO <HE□PA> □EHNH PA □).

Comparative tests of the magnetized needle of the present invention and non-magnetized needle (control) were carried out on degree of pain (A'), degree of sustainment of the pain (B') and induration in the injection part (C') considered to be precursory symptoms of contracture of the Quadriceps femoris caused by injection (vitamins, antibiotics, etc.) needles to reveal that significant effects of 50%, 60% and 80% were obtained on (A'), (B') and (C'), respectively.

The same comparative tests of the needle (D) of the present invention applied with an electrostatic fluid (+) and a control needle (E) free of electrostatic field were effected to obtain significant effects of 20%, 10% and 5% on (A'), (B') and (C'), respectively. When the needle applied with an electrostatic field (−) was used, the significant effects of 5% were obtained on each of (A'), (B') and (C'). When the needle of the present invention having (magnetism+electrostatic field (+)) was used, significant effects of 55%, 65% and 85% were obtained in (A'), (B') and (C'), respectively.

Figure 11:
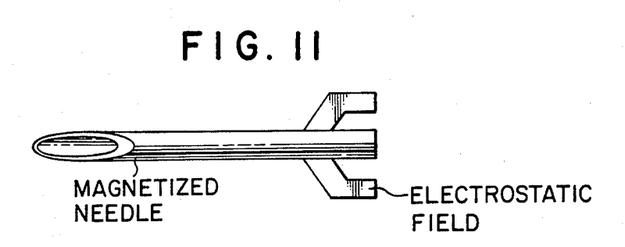
FIG. 11 is a plan view showing the shape of an experimental needle used in experiments according to the present invention.

When a needle having (magnetism+electrostatic field (−)) was used, significant effects of 50%, 60% and 90% were obtained on (A'), and (B') and (C'), respectively. The needles used in those experiments had a shape as shown in FIG. 11.

Figure 9:
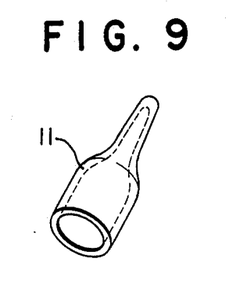
FIG. 9 is a magnetic ampoule.
Figure 10:
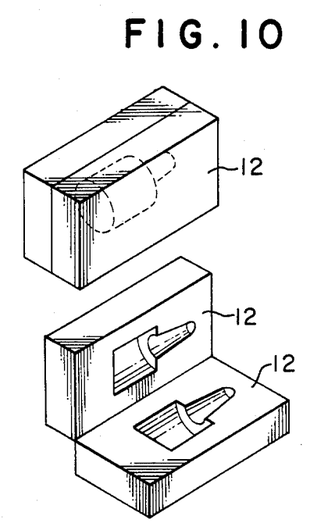
FIG. 10 is a magnetized box for the ampoule.

The present invention further provides a magnetized ampoule for a medicinal liquid to be used for the injection with magnetized needles. This ampoule may be obtained easily by permanently magnetizing an ampoule 11 in FIG. 9 and by placing the ampoule in a magnetized box 12 in FIG. 10 and permanently magnetizing the ampoule.

This ampoule has an effect of increasing the magnetic field effect at the time of the injection with a magnetized needle.

More particularly, the ampoule has an effect of contributing to an increase in physiological activity (particularly, the activity of water) which is an effect of the treatment with the medicinal liquid at the time of injection with the magnetized needle, whereby a complete injection can be expected. As a result of a practical operation, relieving time according to NMR spectrum of bmm/sec./mdl. of a medicinal liquid by a magnetic injection needle of 500 Oe was 0.5–1.0 second, the significant effect being higher than a control by 5%. When the medicinal liquid kept in a magnetized ampoule of 500 Oe for 10 days was used, a significant effect of 10% was obtained in the same operation.

What is claimed is:

1. A needle for acupuncture provided with both a structure in which a magnetic field is formed around the needle and a structure in which an electrostatic field is formed around the needle, a magnet is used as the material for forming the magnetic field and a combination of a corpuscular ray-emissive nuclide and a semiconductor substance is used as the material which is capable of inducing the electrostatic field, said magnet, nuclide and semiconductor substance being fixed at the head of the needle and said nuclide and semiconductor substance being masked in such a manner that the corpuscular ray does not leak out and wherein the masking is made by coating said corpuscular ray-emissive nuclide and said semiconductor substance with a plastic material selected from nylon, rayon, acetate, acryl, polyethylene, teflon and polyvinyl chloride.

2. A needle for acupuncture provided with both a structure in which a magnetic field is formed around the needle and a structure in which an electrostatic field is formed around the needle, a magnet is used as the material for forming the magnetic field and a combination of a corpuscular ray-emissive nuclide and a semiconductor substance is used as the material which is capable of inducing the electrostatic field, said magnet, nuclide and semiconductor substance being fixed at the head of the needle and said nuclide and semiconductor substance being masked in such a manner that the corpuscular ray does not leak out, wherein a gamma-ray emissive nuclide is further fixed with said magnet, said corpuscular ray-emissive nuclide and said semiconductor substance at the head of the needle, so as to emit gamma rays weakly and wherein the masking is made by coating said corpuscular ray-emissive nuclide and said semiconductor substance with a plastic material selected from nylon, rayon, acetate, acryl, polyethylene, teflon and polyvinyl chloride.

* * * * *